United States Patent [19]

Furuya

[11] Patent Number: 5,172,004
[45] Date of Patent: Dec. 15, 1992

[54] METHOD AND APPARATUS FOR MEASURING PARTICLES IN A FLUID

[75] Inventor: Yoshiyuki Furuya, Tokyo, Japan
[73] Assignee: Kowa Company Ltd., Japan
[21] Appl. No.: 695,442
[22] Filed: May 3, 1991

[30] Foreign Application Priority Data

May 8, 1990 [JP] Japan .................................. 2-116903

[51] Int. Cl.$^5$ ............................................ G01N 15/06
[52] U.S. Cl. ...................................... 250/564; 250/574
[58] Field of Search .................... 250/574, 576, 564; 356/336, 337

[56] References Cited

U.S. PATENT DOCUMENTS

| | | | |
|---|---|---|---|
| 4,788,443 | 11/1988 | Furuya | 356/336 |
| 4,842,406 | 6/1989 | Von Bargen | 356/336 |
| 4,850,707 | 7/1989 | Bowen et al. | 356/336 |
| 5,015,094 | 5/1991 | Oka et al. | 356/336 |

Primary Examiner—David C. Nelms
Assistant Examiner—K. Shami
Attorney, Agent, or Firm—Bruce L. Adams; Van C. Wilks

[57] ABSTRACT

Disclosed is a method and apparatus for measuring particles in a fluid by irradiating the fluid containing the particle with a laser beam and deriving particle characteristics such as diameter and size distribution from the intensity of the light scattered by the particles. Based on the value of the output of a photomultiplier used to detect the scattered light, it is determined whether a particle is a fine particle, which is a particle with a photoelectron pulse count that does not exceed a prescribed value, or a large particle, and these particles are counted separately. Fine particles are processed using photon counting, and large particles are processed by an analog process.

17 Claims, 4 Drawing Sheets

METHOD AND APPARATUS FOR MEASURING PARTICLES IN A FLUID

BACKGROUND OF THE INVENTION

1. Field of the Invention

This invention relates to a method and apparatus for measuring particles in a fluid, and more particularly to a method and apparatus for measuring particle characteristics such as the diameter and size distribution of particles in a fluid, by using a laser beam to irradiate the particle-containing fluid as it flows through a measurement cell, detecting the laser light scattered by the particles in the fluid and determining the characteristics from the intensity of the scattered laser light.

2. Description of the Prior Art

As the density level of large-scale integrated memories and other such semiconductor devices continues to rise, going from 4-megabit to 16-megabit, the high-purity water and chemicals used in the semiconductor fabrication processes have to be of the highest quality, containing no impurities. Controlling fine particles in the pure water and chemicals is particularly important as this has a major effect on LSI yield levels.

One way of measuring fine particles in water and chemicals has been to use a scanning electron microscope. However, using a scanning electron microscope has the drawback of being very costly and lacking real-time capabilities. One widespread solution to this has been to use a particle measurement method comprising irradiating the fluid with a laser beam and determining the particle diameter from the intensity of the laser light scattered by the particles.

The theoretical intensity of the Mie scattering of light from a spherical particle in a fluid can be calculated. It is known that the intensity of light scattered by a particle having a diameter that is smaller than one-tenth the wavelength of the incident laser beam will be proportional to the fifth to sixth power of the particle diameter. It therefore follows that a decrease in the particle diameter is accompanied by a weakening in the intensity of the scattered light, and that to be able to detect such weak light it is necessary to use a detection apparatus that has good signal/noise (S/N) ratio characteristics. Single photon counting is an effective method for detecting weak light.

A conventional apparatus utilizing single photon counting will first be explained with reference to FIG. 4. In FIG. 4, a laser beam from a laser light source 1 passes through a lens 2 which focuses the light onto a particle measurement region 4 of a measurement cell 3. The laser light is scattered by particles which pass through the measurement region 4. The light thus scattered by the particles is condensed by a lens 5 to form an image at a slit 6. The scattered light passes through the slit 6 and impinges on a photomultiplier (PM) 7 whereby the scattered light is converted to electrical signals and output as photoelectron pulses. These output signals are amplified by a preamplifier 8 and are then converted to digital signals by a peak discriminator (DISC) 9 and a pulse shaper 10, and the digital signals output from the pulse shaper 10 are then counted by a pulse counter 11 and the count value is stored in a memory 12 in the form of a time series. The time series data stored in the memory 12 is then analyzed by a processor 13, which uses the intensity values of the scattered light to calculate particle diameter and particle concentration.

Use of the single photon counting method makes it possible to eliminate the dark current and fluctuations in the multiplication factor that are causes of noise in the photomultiplier, providing a three- to five-fold improvement in the S/N ratio compared with the usual analog method. With the single photon counting method, the intensity of the scattered light can be measured by counting the number of photoelectron pulses per unit time interval.

However, the number of photoelectron pulses that can be counted per unit time period is limited by the pulse width and the frequency characteristics of the electrical system constituting the photon counters. Photons reaching the photoelectric surface of the photomultiplier cause electrons to be emitted from the same surface by the photoelectric effect. The electrons emitted from the photoelectric surface are multiplied in number within the photomultiplier by a factor of approximately $10^6$. Because of variations in the scanning distance that arise in the course of the electron multiplication in the photomultiplier, each pulse that is output corresponding to the emission of an electron from the photoelectric surface is given a time width.

In the case of side-on type photomultipliers, this time width is usually in the order of 2 ns. Therefore, the emission from the photoelectric surface of electrons at intervals shorter than 2 ns will cause superposing of the photoelectron pulses output by the photomultiplier and make it impossible to count single photons. Even if electrons are emitted at longer intervals than the time width of the photoelectron pulses, the upper count per unit time period is limited by the frequency characteristics of the electrical system constituting the photon counters.

Thus, the three- to five-fold improvement in the S/N ratio compared with analog methods enables smaller particles to be measured with the single photon counting method, with this method however the dynamic range is limited by the time width of the photoelectron pulses and the frequency characteristics of the electrical system of the photon counters to a count rate of about $10^8$ per second and cannot be used to accurately determine the intensity of high-intensity scattered light from large particles.

SUMMARY OF THE INVENTION

An object of the present invention is to solve these drawbacks of the prior art and to provide a method and apparatus for measuring particles in a fluid which enable various characteristics of particles in a fluid to be determined with good accuracy regardless of the size of the particles.

According to the present invention there is provided a method for measuring particles in a fluid flowing in a measurement cell by irradiating the fluid containing the particles with a laser beam, detecting the laser light scattered by the particles and using the intensity of the scattered light to derive the diameter and size distribution of the particles, the method comprising determining from the value of a signal output by a photomultiplier that detects scattered light from particles whether or not a particle is a fine particle that does not exceed a prescribed value, and determining particle diameter and size distribution by using single photon counting when particles are determined as being fine particles with a photoelectron pulse count that does not exceed a prescribed value and by using analog processing when particles exceed the prescribed value. The present invention also comprises an apparatus for measuring particles in a fluid flowing in a measurement cell by irradiating the fluid containing the particles with a laser beam, detecting the laser light scattered by the particles and using the intensity of the scattered light to derive the diameter and size distribution of the particles, the apparatus comprising a photomultiplier for detecting light scattered by particles, means for counting photoelectron pulses corresponding to signals output by the photomultiplier, means for analyzing the analog pulse height of amplified signals from the photomultiplier, means for discriminating whether or not measured particles are fine particles with a photoelectron pulse count that does not exceed a prescribed value, and processor means for calculating particle diameter and size distribution based on signals from the counting or analyzing means, wherein the diameter and size distribution of particles are derived by the calculating processor means by counting the photoelectron pulses in the case of particles determined as being fine particles giving rise to a photoelectron pulse count that does not exceed a prescribed value, and by using analog processing for signal counts from the analyzing means in the case of particles determined as being large particles giving rise to a count that exceeds the prescribed value.

This arrangement thus enables a fine particle to be analyzed in terms of its scattered intensity using the single photon counting method, and a large particle to be analyzed using the analog processing method, thus improving the detection sensitivity and enlarging a dynamic range.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENTS

Embodiments of the invention will now be described in detail with reference to the drawings.

Figure 1:
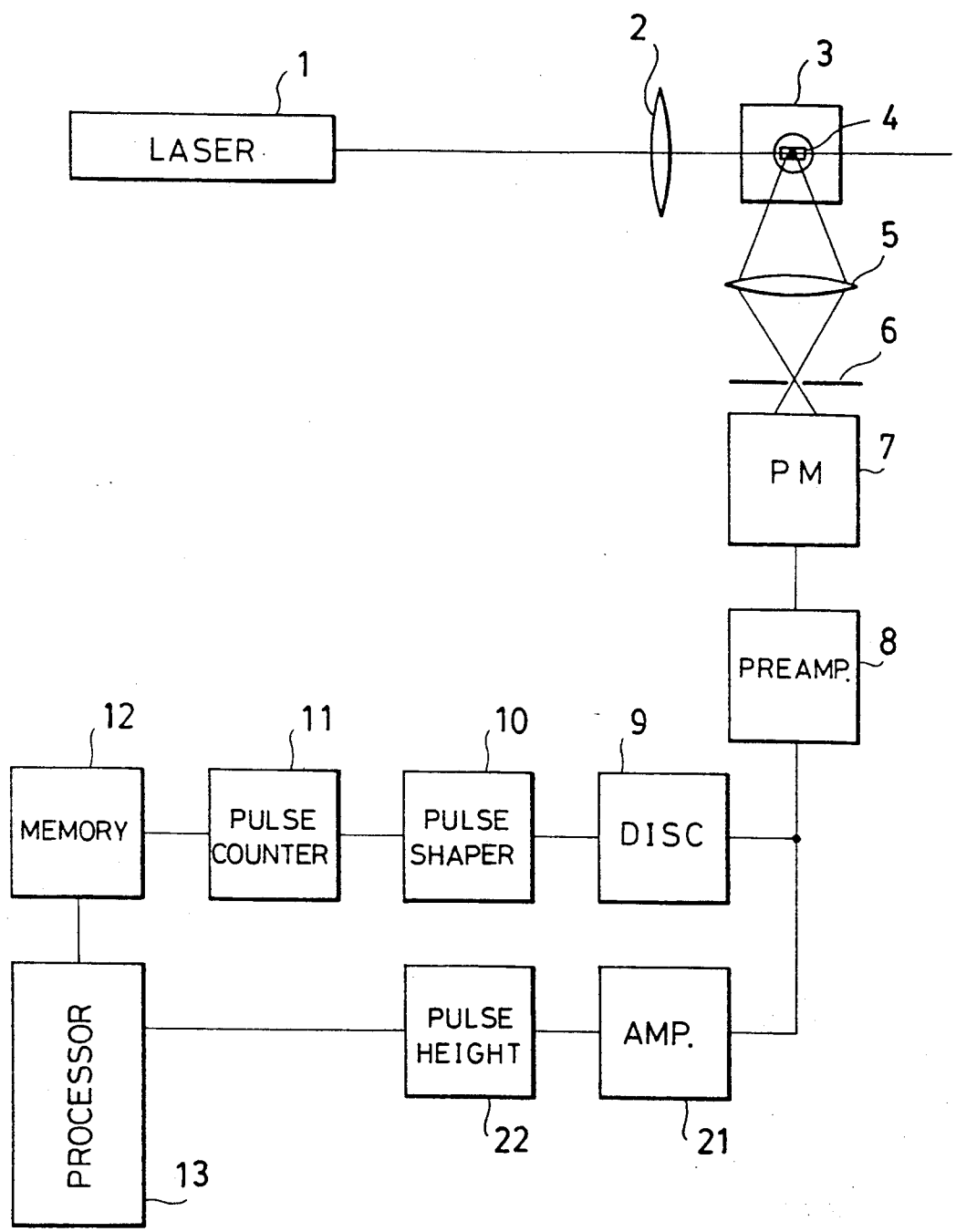
FIG. 1 is a block diagram illustrating the structure of the apparatus according to an embodiment of the present invention.
Figure 4:
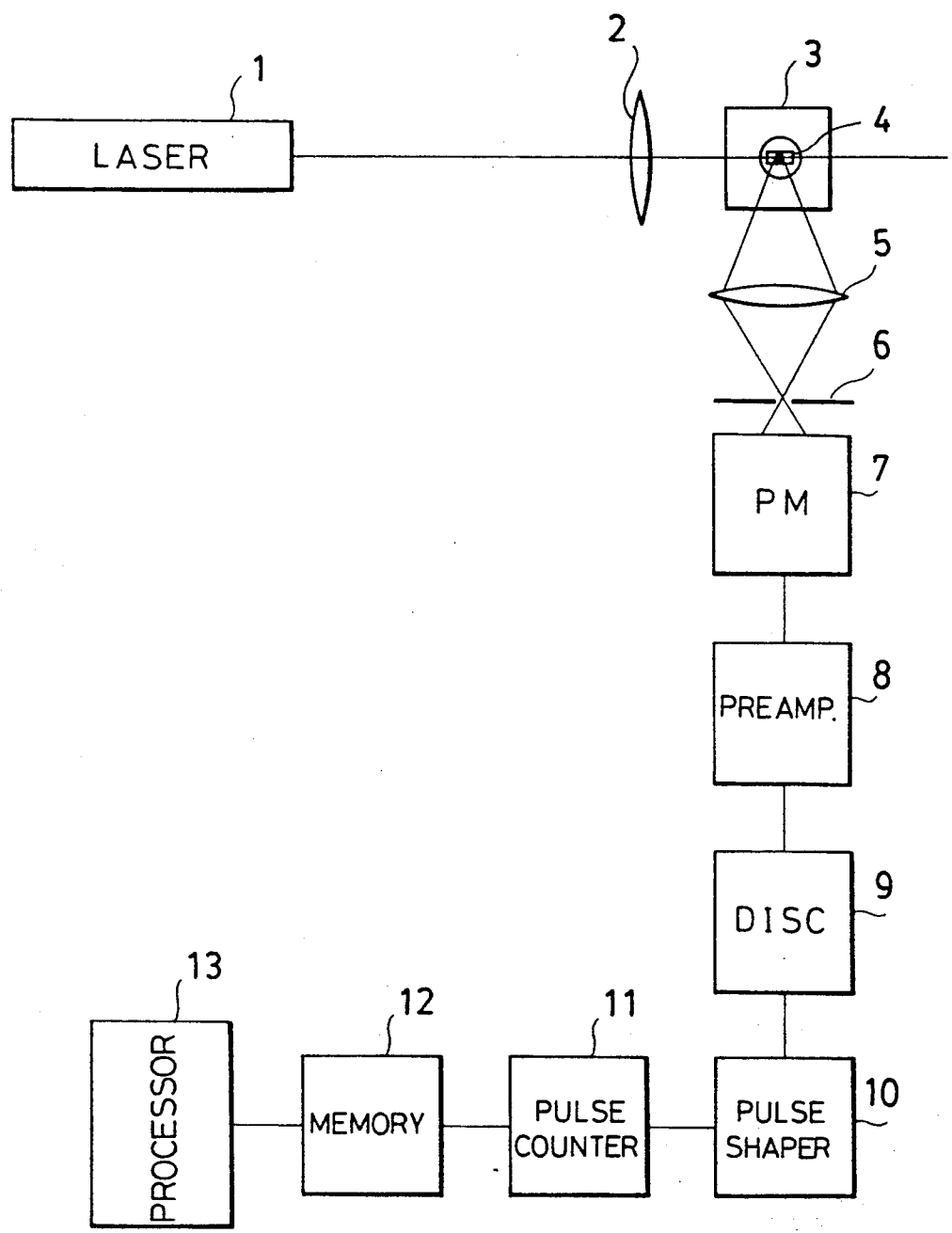
FIG. 4 is a block diagram illustrating the structure of a prior art apparatus.

The structure of a first embodiment of the apparatus according to the invention is shown in FIG. 1. Components thereof that are identical with those in FIG. 4 are denoted by like reference numerals and will not be explained again here.

With reference to FIG. 1, signals received from a photomultiplier 7 and amplified by a preamplifier 8 are split, with one side being subjected to signal processing by a conventional single photon counting method or procedure. An amplifier 21 and an analog pulse height analyzer 22 are provided for subjecting the other side to analog processing when the intensity of the scattered light is too high for photon counting. The preamplifier 8 should have frequency characteristics that match the time width of the photoelectron pulses (about $10^{-9}$ seconds), but the amplifier 21 only needs to have a frequency characteristic that can match the time period it takes the laser beam to sweep a particle (about $10^{-3}$ seconds). The method used for signal processing by single photon counting is the same as the conventional one. The analog pulse height of signals amplified by the amplifier 21 and each having the time width of the passage of a particle through the laser beam is analyzed by the analog pulse height analyzer 22 and the particle size distribution is derived by a processor 13.

The processor 13 determines whether or not the signal pulse count value counted by a pulse counter 11 is equal to or below a prescribed value. If the count value is equal to or below the prescribed value, the measured particle is determined as being a fine particle and the single photon counting procedure is used to calculate particle diameter and size distribution. If the count value exceeds the prescribed value, particle diameter and size distribution are calculated using an analog method or procedure based on the signal output of the analog pulse height analyzer 22.

Figure 2:
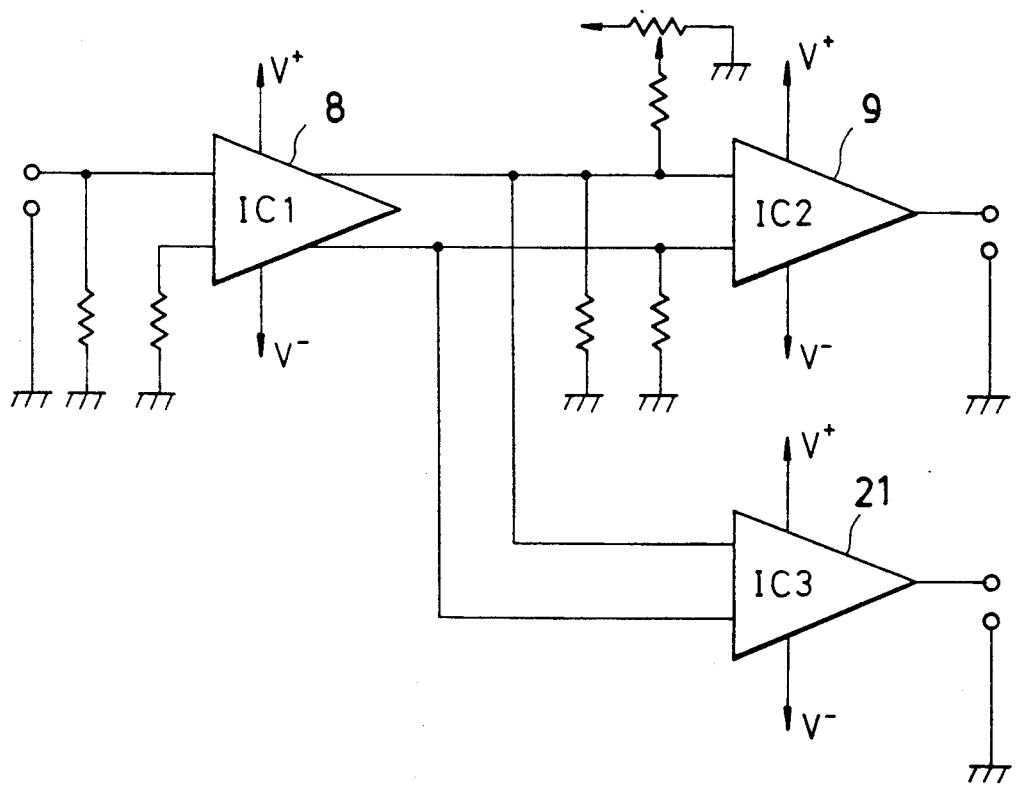
FIG. 2 is a more detailed diagram of the circuit arrangement of the apparatus of FIG. 1.

FIG. 2 shows one example which realizes the embodiment in accordance with the present invention. IC1 denotes a preamplifier 8 for amplifying the signal from the photomultiplier 7, and IC2 an analog pulse height discriminator a for processing the signal according to the single photon counting method. IC3 denotes an amplifier 21 for amplifying the signal from the preamplifier IC1 and for producing a signal to the analog pulse height discriminator 22 in FIG. 1 for analog signal processing.

Figure 3A:
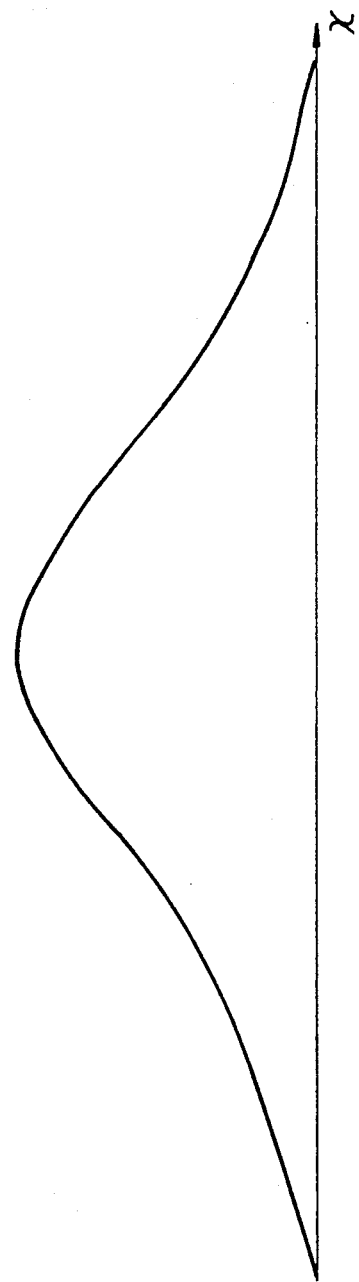
FIGS. 3a to 3d are signal waveform diagrams for explaining the operation of the apparatus illustrated in FIG. 1.

The operation of the apparatus will now be explained. A laser light source emits a light beam having a space intensity distribution such as the one illustrated by FIG. 3a. This laser beam irradiates particles that flow through the measurement zone 4 of a measurement cell 3. In the TEM00 mode the space intensity distribution of the laser light is Gaussian. When a particle of a given velocity passes through such a beam, the time envelope of the scattered light intensity from the particle will reflect the space intensity distribution of the laser beam.

Figure 3B:
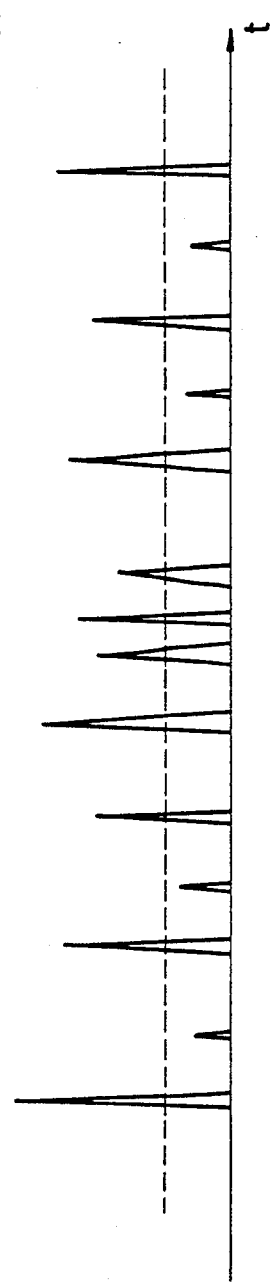

FIG. 3b shows time-based changes in a signal output by the photomultiplier 7 when a fine particle passes through the laser beam. Because of the weak nature of the scattered light from the fine particle, the photoelectron pulses become dispersed, with no overlapping.

Figure 3C:
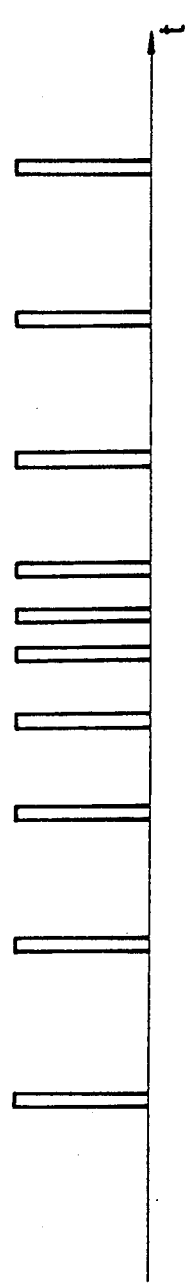

FIG. 3c shows the digitized signal produced by a wave height discriminator 9 from a signal with an amplitude exceeding the level represented in FIG. 3b by the broken line. Digitizing makes it possible to remove dark current components with a smaller amplitude than the broken-line level and also eliminates fluctuation in the multiplication factor of the photomultiplier. Digital pulses that have been pulse height discriminated are counted in the pulse counter 11 and stored as time-series measurement data in a memory 12.

Figure 3D:

FIG. 3d shows time-based changes in a signal output by the photomultiplier 7 when a large particle passes through the laser beam. The high intensity of scattered light produced by large particles, especially when the particle passes through the center of the beam, causes superposing of photoelectron pulses. This kind of photoelectron pulse increases the count value by the pulse counter 11, and the processor 13 determines whether or not this pulse count value of the pulse counter 11 is equal to or below the prescribed value. If the pulse count value does not exceed the prescribed value, the processor 13 determines the measured particle is a fine particle and the single photon counting procedure is used to calculate particle diameter and size distribution based on the data stored in the memory 12.

If the pulse count value output by the pulse counter 11 exceeds the prescribed value, meaning that the measured particles are large ones such as the ones that produced the waveform shown in FIG. 3d, the particle diameter and size distribution are derived by applying a prescribed operation expression using an analog method based on the signal output of the analog pulse height analyzer 22.

In the embodiment described above, a processor is used to determine whether photoelectron pulse count values do or do not exceed the prescribed values, but a determination circuit or discriminator that is separate from the processor may be used for this purpose.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. A method for measuring particles in a fluid flowing in a measurement cell by irradiating the fluid containing the particles with a laser beam, detecting the laser light scattered by the particles and using the intensity of the scattered light to derive the diameter and size distribution of the particles, comprising the steps of:
   determining from the value of a signal output by a photomultiplier that detects scattered light from particles whether or not a particle is a fine particle that does not exceed a prescribed size; and
   deriving particle diameter and size distribution by using photon counting when the particles are determined as being fine particles with a photoelectron pulse count that does not exceed a prescribed value, and by using analog processing when the particles are determined as exceeding the prescribed size.

2. An apparatus for measuring particles in a fluid flowing in a measurement cell by irradiating the fluid containing the particles with a laser beam, detecting the laser light scattered by the particles and using the intensity of the scattered light to derive the diameter and size distribution of the particles, comprising:
   a photomultiplier for detecting light scattered by particles;
   means for counting photoelectron pulses corresponding to signals output by the photomultiplier;
   means for analyzing the analog pulse height of amplified signals from the photomultiplier;
   means for discriminating whether or not measured particles are fine particles based on a photoelectron pulse count that does not exceed a prescribed value; and
   processor means for calculating particle diameter and size distribution based on signals from the counting or analyzing means;
   wherein the diameter and size distribution of particles are derived by the processor means by counting the photoelectron pulses in the case of particles determined as being fine particles corresponding to a photoelectron pulse count that does not exceed a prescribed value, and by using analog processing for signal counts from the analyzing means in the case of particles determined as being large particles corresponding to a count that exceeds the prescribed value.

3. An apparatus as set forth in claim 2, wherein the processor means includes the means for discriminating.

4. A method as set forth in claim 1, wherein the prescribed value is indicative of particle size.

5. A method for analyzing the size of particles in a flowing fluid, comprising the steps of:
   flowing a fluid containing particles through a measuring cell;
   irradiating the fluid in the measuring cell with a laser beam to cause the laser light to be scattered by the particles;
   detecting the scattered laser light and providing an output signal indicative of the intensity of the scattered light;
   determining from the output signal whether or not a particle is larger or smaller than a predetermined size;
   analyzing the size of the particles, based on the output signal, by photon counting in response to a determination that the particles are smaller than said predetermined size; and
   analyzing the size of the particles, based on the output signal, by analog processing in response to a determined that the particles are larger than said predetermined size.

6. A method according to claim 5; wherein the analyzing steps include deriving particle diameter and size distribution data based on the output signal.

7. A method according to claim 5; wherein the determining step comprises deriving from the output signal a pulse signal having a pulse number representative of particle size, counting the number of pulses in the pulse signal and producing a pulse count value, and comparing the pulse count value with a prescribed value to determine whether or not a particle is larger or smaller than a predetermined size.

8. A method according to claim 7; wherein the analyzing steps include deriving particle diameter and size distribution data based on the output signal.

9. An apparatus for measuring particles in a fluid, comprising: a measurement cell through which a fluid containing particles to be measured flows during use of the apparatus; means for irradiating the fluid in the measurement cell with laser light such that the particles in the fluid scatter the laser light; means for photoelectrically detecting the scattered laser light and producing an electrical pulse signal corresponding to the intensity of the scattered laser light; first means responsive to the electrical pulse signal for deriving therefrom a first signal composed of a series of pulses whose number corresponds to the scattered light intensity and for counting the pulses and providing a pulse count value per unit time; second means responsive to the electrical pulse signal for deriving therefrom a second signal representative of the analog pulse height of the electrical pulse signal; and processing means responsive to the first and second signals for deriving particle size data based on the first signal when the pulse count value does not exceed a prescribed value and for deriving particle size data based on the second signal when the pulse count value exceeds said prescribed value.

10. An apparatus according to claim 9; wherein the processing means includes means for calculating particle size data in accordance with a photon counting procedure using the first signal and in accordance with an analog procedure using the second signal.

11. An apparatus according to claim 10; wherein the means for photoelectrically detecting comprises a photomultiplier for detecting the scattered laser light and producing an electrical signal comprised of photoelectric pulses.

12. An apparatus according to claim 11; wherein the first means includes means for digitizing the electrical pulse signal to produce the first signal, and pulse counting means for counting the pulses of the first signal.

13. An apparatus according to claim 12; wherein the second means includes a pulse height analyzer for analyzing the analog pulse height of the electrical pulse signal to produce the second signal.

14. An apparatus according to claim 10; wherein the processing means includes means for calculating particle size data including particle diameter and size distribution.

15. An apparatus according to claim 9; wherein the means for photoelectrically detecting comprises a photomultiplier for detecting the scattered laser light and producing an electrical signal comprised of photoelectric pulses.

16. An apparatus according to claim 16; wherein the first means includes means for digitizing the electrical pulse signal to produce the first signal, and pulse counting means for counting the pulses of the first signal.

17. An apparatus according to claim 16; wherein the second means includes a pulse height analyzer for analyzing the analog pulse height of the electrical pulse signal to produce the second signal.

* * * * *